(12) United States Patent
Kumura et al.

(10) Patent No.: US 11,512,091 B2
(45) Date of Patent: Nov. 29, 2022

(54) CRYSTAL OF BENZOXAZOLE DERIVATIVE

(71) Applicant: MEIJI SEIKA PHARMA CO., LTD., Tokyo (JP)

(72) Inventors: Ko Kumura, Kanagawa (JP); Keiji Tamura, Tokyo (JP); Takashi Watanabe, Kanagawa (JP); Michiko Takahashi, Kanagawa (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 201 days.

(21) Appl. No.: 17/255,584

(22) PCT Filed: Jun. 27, 2019

(86) PCT No.: PCT/JP2019/025512
§ 371 (c)(1),
(2) Date: Dec. 23, 2020

(87) PCT Pub. No.: WO2020/004517
PCT Pub. Date: Jan. 2, 2020

(65) Prior Publication Data
US 2021/0155630 A1    May 27, 2021

(30) Foreign Application Priority Data
Jun. 27, 2018 (JP) .............................. JP2018-121413

(51) Int. Cl.
*C07D 487/08* (2006.01)

(52) U.S. Cl.
CPC ........ *C07D 487/08* (2013.01); *C07B 2200/13* (2013.01)

(58) Field of Classification Search
CPC .................. C07D 487/08; C07B 2200/13
See application file for complete search history.

(56) References Cited

U.S. PATENT DOCUMENTS

| | | |
|---|---|---|
| 2012/0028974 A1 | 2/2012 | Nielsen et al. |
| 2016/0159783 A1 | 6/2016 | Kikuchi et al. |
| 2019/0322686 A1 | 10/2019 | Tamura et al. |

FOREIGN PATENT DOCUMENTS

| | | |
|---|---|---|
| EP | 3020718 A1 | 5/2016 |
| JP | 2012-512192 | 5/2012 |
| WO | 2015/005429 | 1/2015 |
| WO | 2018/124060 | 7/2018 |
| WO | 2020/004521 | 1/2020 |

OTHER PUBLICATIONS

International Search Report dated Sep. 17, 2019 issued in International Patent Application No. PCT/JP2019/025512.
Written Opinion of the International Search Authority dated Sep. 17, 2019 issued in International Patent Application No. PCT/JP2019/025512.
Extended European Search Report dated Nov. 17, 2021 for corresponding European application No. 19826594.4.

*Primary Examiner* — Timothy R Rozof
(74) *Attorney, Agent, or Firm* — Carmody Torrance Sandak & Hennessey LLP

(57) ABSTRACT

Provided are crystals of 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol represented by formula (1),

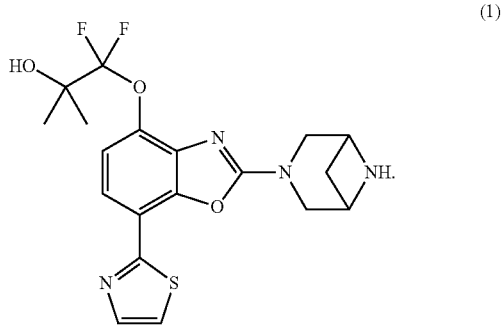

(1)

7 Claims, 2 Drawing Sheets

CRYSTAL OF BENZOXAZOLE DERIVATIVE

TECHNICAL FIELD

The present invention relates to crystals of 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol having a phosphodiesterase (PDE) 4 inhibiting action.

BACKGROUND ART

Pharmaceutical drugs are required to have uniform qualities and storage stability in addition to efficacy to diseases and safety. Hence, drug substances of pharmaceutical drugs are required to have an excellent stability to temperature, humidity, and light.

There has been no report that a compound having an excellent PDE4 inhibiting action and an excellent stability to temperature, humidity, and light has been provided.

SUMMARY OF INVENTION

Technical Problem

The present invention has an object to provide a drug substance suitable as a pharmaceutical drug, using a compound having an excellent PDE4 inhibiting activity.

Solution to Problem

As a result of conducting earnest studies in order to solve the problem described above, the present inventors have succeeded in crystallization of a compound represented by formula (1) and having a chemical stability, and discovered two different crystal forms (an I type crystal and an II type crystal).

The I type crystal and the II type crystal of the compound represented by formula (1) have a sufficient chemical stability in a thermal stability test, a photostability test, and an accelerated stability test.

That is, the present invention relates to a crystal of 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol represented by formula (1) (a compound represented by formula (1)),

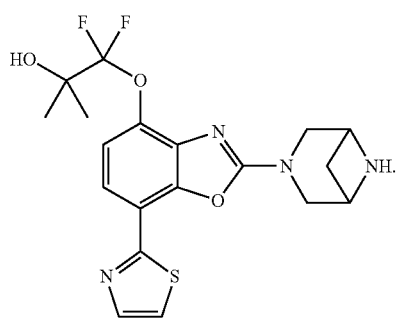

(1)

Advantageous Effects of Invention

The crystals of the present invention can provide drug substances suitable as pharmaceutical drugs.

The crystals of the compound represented by formula (1) according to the present invention are useful for treatment or prevention, or both of diseases attributable to PDE4 or various diseases relating to PDE4, because the crystals have an excellent PDE4 inhibiting activity. Examples of the diseases attributable to PDE4 or the diseases relating to PDE4 include: various fibrosis diseases such as asthma, COPD, interstitial pneumonia, idiopathic pulmonary fibrosis, systemic sclerosis, and nonalcoholic steatohepatitis; inflammatory bowel diseases such as Crohn's disease and ulcerative colitis; multiple sclerosis; rheumatism; ankylosing spondylitis; acne; atopic dermatitis; alopecia areata; allergic conjunctivitis; dry eye syndrome; rhinitis; psoriasis arthritis; psoriasis vulgaris; sarcoidosis; Behçet's disease; systemic lupus erythematosus; depression; cognitive impairment; Parkinson's disease; Alzheimer's disease; Huntington's disease; schizophrenia; muscular dystrophy; vitiligo; hidradenitis suppurativa; lichen planus; various cancers (e.g., colorectal cancer, lung cancer, hematological cancer, and brain tumor); and metabolic diseases (e.g., diabetes and obesity). Moreover, the crystals of the compound represented by formula (1) have properties suitable as pharmaceutical drugs, such as solubility, hygroscopicity, and solution stability.

DESCRIPTION OF EMBODIMENTS

Figure 1:
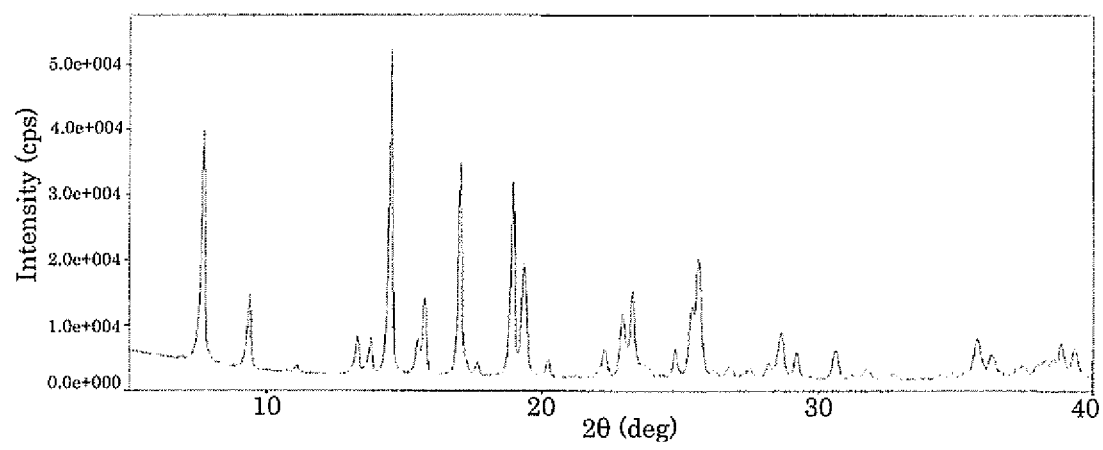
FIG. 1 plots a powder X-ray diffraction pattern of the I type crystal of the compound represented by formula (1)

Crystal polymorphism is formation of two or more types of crystals by a compound. Generally, it is known that different crystal forms of crystal polymorphs may be different in stability and physical properties. Further, when there are crystal polymorphs, crystal transition may generally occur. Crystal transition is a phenomenon often observed in, for example, drying, grinding, and storage in chemical industries. Crystals that do not undergo crystal transition to another crystal form are suitable as drug substances of pharmaceutical drugs. Hence, when a plurality of crystal forms are obtained, it is important to validate the stability of each.

In the present specification, two different crystal forms are referred to as I type crystal and II type crystal respectively.

The present invention relates to crystals of 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol (the compound represented by formula (1)), and pharmaceutical compositions containing the crystals. The compound represented by formula (1) can be produced by the method described in International Publication No. WO 2018/124060 (International Application No. PCT/JP2017/046610). However, the producing method is not limited to the method.

In the present invention, the I type crystal has characteristic peaks at diffraction angles (2θ±0.2°) of 7.7°, 14.5°, 17.0°, 18.9°, 19.4°, 23.3°, and 25.7° in powder X-ray diffraction, and has an endothermic peak temperature of 205±3° C. in differential scanning calorimetry (DSC). Preferably, the I type crystal has characteristic peaks at diffraction angles (2θ±0.2°) of 7.7°, 9.4, 13.2°, 13.7°, 14.5°, 15.7°, 17.0°, 18.9°, 19.4°, 22.9°, 23.3°, 25.7°, 28.7°, and 35.7° in powder X-ray diffraction, and has an endothermic peak temperature of 205±3° C. in differential scanning calorimetry (DSC).

In the present invention, the II type crystal has characteristic peaks at diffraction angles (2θ±0.2°) of 7.8°, 14.7°, 15.7°, 19.3°, and 25.0° in powder X-ray diffraction. Preferably, the II type crystal has characteristic peaks at diffraction angles (2θ±0.2°) of 7.4°, 7.8°, 8.2°, 12.7°, 13.6°, 14.3°, 14.7°, 15.7°, 16.5°, 19.3°, 22.1°, 25.0°, and 25.6° in powder X-ray diffraction.

The crystals can be distinguished from each other by, for example, powder X-ray diffraction. Values of diffraction angles in powder X-ray diffraction may contain errors in the range of ±0.2° due to, for example, difference in instruments and difference in analyzing methods. Further, relative intensities of the peaks in powder X-ray diffraction may vary depending on difference in, for example, crystal habits or sampling conditions. In powder X-ray diffraction, diffraction angles and the overall pattern are important for identification of crystals, and they may slightly vary depending on the measurement conditions. Moreover, values of endothermic peak temperatures in differential scanning calorimetry (DSC) may contain errors in the range of ±3° C. due to, for example, difference in instruments and difference in sample amounts. Also in differential scanning calorimetry (DSC), the overall pattern is important for identification of crystals, and it may slightly vary depending on the measurement conditions. An endothermic peak temperature in differential scanning calorimetry (DSC) is the temperature of the peak top of an endothermic peak.

The I type crystal can be produced by various methods, and can be produced by the following method.

The I type crystal can be obtained by crystallizing the compound represented by formula (1), which is obtained by the method described in International Publication No. WO 2018/124060 (International Application No. PCT/JP2017/046610), in, for example, one solvent selected from, or a mixture solvent of two or more selected from alcohol solvents, ester solvents, halogen solvents, or water. The amount of the solvent is not particularly limited and is preferably, for example, an amount (v/w) that is from 1 time through 200 times greater than the weight of the compound represented by formula (1). The temperature is not particularly limited, and is preferably, for example, from 10° C. through the reflux temperature of the solvent used. In crystallization, a solution of the compound represented by formula (1) in the solvent described above is subjected to one or more operations selected from cooling, concentration, addition of an alcohol solvent, addition of an ester solvent, addition of a mixture solvent, addition of an aliphatic hydrocarbon solvent, or addition of water. The cooling temperature is not particularly limited and is preferably, for example, from −10° C. through 10° C. Concentration is not particularly limited and is preferably to, for example, an amount (v/w) that is from 1 time through 10 times greater than the weight of the compound represented by formula (1). The amount of an alcohol solvent, an ester solvent, a mixture solvent, an aliphatic hydrocarbon solvent, and water is not particularly limited and is preferably, for example, an amount (v/w) that is from 0.01 times through 100 times greater than the weight of the compound represented by formula (1). Next, with an alcohol solvent or an ester solvent, or a mixture solvent thereof added, the obtained crystal may be heated and allowed to cool.

The II type crystal can be produced by various methods, and can be produced by the following method.

The II type crystal can be obtained by dissolving the compound represented by formula (1), which is obtained by the method described in International Publication No. WO 2018/124060 (International Application No. PCT/JP2017/046610), in, for example, one solvent selected from, or a mixture solvent of two or more selected from alcohol solvents, ester solvents, halogen solvents, or water, and subsequently cooling and crystallizing the compound. The amount of the solvent is not particularly limited and is preferably, for example, an amount (v/w) that is from 1 time through 200 times greater than the weight of the compound represented by formula (1). The temperature for dissolving the compound represented by formula (1) is not particularly limited and is preferably, for example, from 10° C. through the reflux temperature of the solvent used. Cooling for crystallization is not particularly limited, is preferably at from −30° C. through 10° C., and is preferably rapid cooling. Next, the suspension in which a crystal is precipitated through the cooling may be subjected to one or more operations selected from concentration, addition of an alcohol solvent, addition of an ester solvent, addition of a mixture solvent, addition of an aliphatic hydrocarbon solvent, or addition of water. Concentration is not particularly limited and is preferably to, for example, an amount (v/w) that is from 1 time through 10 times greater than the weight of the compound represented by formula (1). The amount of an alcohol solvent, an ester solvent, a mixture solvent, an aliphatic hydrocarbon solvent, and water is not particularly limited and is preferably, for example, an amount (v/w) that is from 0.01 times through 100 times greater than the weight of the compound represented by formula (1).

Alcohol solvents are, for example, methanol, ethanol, 2-propanol, and n-butanol. Methanol, ethanol, or 2-propanol is preferable. One of these alcohol solvents may be used alone or two or more of these alcohol solvents may be used in combination.

Ester solvents are, for example, methyl formate, ethyl formate, methyl acetate, ethyl acetate, and isopropyl acetate. One of these ester solvents may be used alone or two or more of these ester solvents may be used in combination.

Halogen solvents are, for example, dichloromethane, chloroform, and 1,2-dichloroethane. One of these halogen solvents may be used alone or two or more of these halogen solvents may be used in combination.

Aliphatic hydrocarbon solvents are, for example, pentane, hexane, cyclohexane, and heptane. Hexane or heptane is preferable. One of these aliphatic hydrocarbon solvents may be used alone or two or more of these aliphatic hydrocarbon solvents may be used in combination.

Mixture solvents are, for example, mixture solvents of one or more selected from alcohol solvents, ester solvents, halogen solvents, aliphatic hydrocarbon solvents, or water. A mixture solvent of methanol and ethyl acetate, ethanol and ethyl acetate, 2-propanol and ethyl acetate, or hexane and ethyl acetate is preferable. The range of the ratio of the mixture solvent is from 1/10 through 10/1 (v/v), and preferably from 1/2 through 2/1 (v/v).

EXAMPLES

The present invention will be specifically described below by way of Examples. However, the scope of the present invention should not be construed as being limited to these Examples.

In powder X-ray diffraction, SMARTLAB available from Rigaku Corporation (with a radiation source: CuKα, a wavelength: 1.541862 angstroms, a scan speed: 1.0039°/minute, a step width: 0.0100°, an X-ray output: 40 kV 30 mA, and a measurement temperature: room temperature) was used. In differential scanning calorimetry (DSC), Q200 available from TA Instruments Japan Inc. (with a temperature raising rate: 5° C./minute, a nitrogen flow rate: 50 mL/minute, and a pan: simple sealing) was used.

The compound represented by formula (1) can be obtained by the method described in International Publication No. WO 2018/124060 (International Application No. PCT/JP2017/046610) and presented below.

Referential Synthesis Example 1

Synthesis of the Compound Represented by Formula (1)

(Step 1) (((2-Nitro-1,3-phenylene)bis(oxy))bis(methylene))dibenzene

2-Nitroresorcinol (5 g) was dissolved in N,N-dimethylformamide (88 mL), benzyl bromide (8.4 mL, an equivalent amount of 2.2) and cesium carbonate (25 g, an equivalent amount of 2.4) were added to the resultant, and the resultant was stirred at room temperature for 12 hours. Ethyl acetate was added to the reaction liquid, the organic layer was washed with a 1% hydrochloric acid aqueous solution, and the organic layer was again washed with distilled water. The organic layer was dried with anhydrous magnesium sulfate and then filtrated. Hexane was added to a residue obtained by vacuum concentration of the filtrate, and a precipitated solid was taken out as a filtrand, to obtain the entitled compound (10 g).

(Step 2) 3-(Benzyloxy)-2-nitrophenol

The compound (10 g) obtained in the step 1 was dissolved in dichloromethane (270 mL), a 1.0 M heptane solution (45 mL, an equivalent amount of 1.5) of boron trichloride was added to the resultant at −78° C., and the resultant was stirred at −78° C. for 1 hour. Methanol was added to the reaction liquid for 10 minutes, the resultant was heated to room temperature, and distilled water was added to the resultant. The resultant mixture was subjected to extraction with dichloromethane twice, and the organic layer was dried with anhydrous magnesium sulfate. The resultant was filtrated. A residue obtained by vacuum concentration of the filtrate was refined by silica gel column chromatography (with hexane: ethyl acetate at 9.5:0.5), to obtain the entitled compound (4.7 g).

(Step 3) 3-(Benzyloxy)-6-bromo-2-nitrophenol

Acetonitrile (41 mL), chlorotrimethyl silane (0.16 mL, an equivalent amount of 0.1), and N-bromosuccinimide (2.2 g, an equivalent amount of 1.0) were added to the compound (3.0 g) obtained in the step 2, and the resultant was stirred at room temperature for 1 hour. Water was added to the reaction liquid at 0° C., the resultant was subjected to extraction with ethyl acetate, and then the organic layer was dried with anhydrous magnesium sulfate. After the resultant was filtrated, a residue obtained by vacuum concentration of the filtrate was refined by silica gel column chromatography (with hexane: ethyl acetate at 7:3), to obtain the entitled compound (3.1 g).

(Step 4) 2-Amino-3-(benzyloxy)-6-bromophenol

A solution (37 mL) of the compound (3.1 g) obtained in the step 3 in ethanol was dropped into a solution (63 mL) of sodium dithionite (3.1 g, an equivalent amount of 8) in water at 0° C. After the resultant became room temperature, water (30 mL) and ethanol (18 mL) were added to the resultant, and the resultant was stirred for 1 hour and 20 minutes. The reaction liquid was filtrated and washed with ethanol. Water (67 mL) was added at 0° C. to a residue obtained by vacuum concentration of the filtrate, and the resultant was stirred. A solid was taken out as a filtrand, washed with distilled water and ethyl acetate, and subjected to vacuum drying, to obtain the entitled compound (3.3 g).

(Step 5) 4-(Benzyloxy)-7-bromobenzo[d]oxazole-2-thiol

The compound (3.3 g) obtained in the step 4 was dissolved in ethanol (15 mL), an ethanol solution (35 mL) of 0.5 M potassium hydroxide and carbon disulfide (2.9 mL, an equivalent amount of 5) were added to the resultant, and the resultant was heated at 50° C. for 1 hour and 20 minutes. After the resultant became room temperature, water (68 mL) and a 5M hydrochloric acid (6 mL) were added to the resultant. A solid was taken out as a filtrand, to obtain the entitled compound (2.3 g).

(Step 6) tert-butyl 3-(4-(benzyloxy)-7-bromobenzo[d]oxazol-2-vi)-3,6-diazabicyclo[3.1.1]heptane-6-carboxylate m-Xylene (17 mL) was added to the compound (2.3 g) obtained in the step 5 and tert-butyl 3,8-diazabicyclo[3.2.1]octane-8-carboxylate (1.5 g, an equivalent amount of 1.1), and the resultant was stirred at 120° C. overnight. A 1N sodium hydroxide aqueous solution (20 mL) was added to the resultant, and the resultant was subjected to extraction with ethyl acetate. The organic layer was dried with anhydrous magnesium sulfate, and then the resultant was filtrated. A residue obtained by vacuum concentration of the filtrate was refined by silica gel column chromatography (from hexane:ethyl acetate=50:1 to hexane:ethyl acetate=7:3), to obtain the entitled compound (2.9 g).

(Step 7) tert-butyl 3-(4-(benzyloxy)-7-(thiazol-2-yl)benzo[d]oxazol-2-yl)-3,6-diazabicyclo[3.1.1]heptane-6-carboxylate Toluene (19 mL) was added to the compound (2.9 g) obtained in the step 6, a 0.5 M tetrahydrofuran solution (29 mL, an equivalent amount of 2.5) of 2-thiazolyl zinc bromide and a 1,1'-bis(diphenylphosphino)ferrocene palladium (II) dichloride/dichloromethane complex (480 mg, an equivalent amount of 0.1) were added to the resultant, and the resultant was stirred under an argon atmosphere at 90° C. for 6 hours. Saturated sodium bicarbonate water was added to the reaction liquid, and the resultant was subjected to celite filtration. After the filtrate was subjected to extraction with ethyl acetate, the organic layer was dried with anhydrous magnesium sulfate. After the resultant was filtrated, a residue obtained by vacuum concentration of the filtrate was refined by silica gel column chromatography (from hexane:ethyl acetate=9:1 to hexane:ethyl acetate=1:1), to obtain the entitled compound (2.5 g).

(Step 8) tert-butyl 3-(4-hydroxy-7-(thiazol-2-yl)
benzo[d]oxazol-2-yl)-3,6-diazabicyclo[3.1.1]hep-
tane-6-carboxylate The compound (1.5 g) obtained in the step 7 was dissolved in tetrahydrofuran (60 mL), 20% palladium hydroxide/carbon (with a water content of 50%) (2.5 g) was added to the resultant under an argon atmosphere, and the resultant was filled with hydrogen and stirred at 50° C. for 4.5 hours. The reaction liquid was subjected to celite filtration, a residue obtained by vacuum concentration of the filtrate was refined by silica gel column chromatography (from chloroform to chloroform:methanol=94:6), to obtain the entitled compound (1.0 g).

(Step 9) tert-butyl 3-(4-(2-ethoxy-1,1-difluoro-2-
oxoethoxy)-7-(thiazol-2-yl)benzo[d]oxazol-2-yl)-3,
6-diazabicyclo[3.1.1]heptane-6-carboxylate The compound (1.0 g) obtained in the step 8 was dissolved in acetonitrile (24 mL), 1,8-diazabicyclo[5.4.0]un-dec-7-ene (3.6 mL, an equivalent amount of 10) and ethyl 2-bromo-2,2-difluoroacetate (3.1 mL, an equivalent amount of 10) were added to the resultant, and the resultant was stirred at room temperature for 2 hours. A saturated ammonium chloride aqueous solution was added to the reaction liquid, and the resultant was subjected to extraction with ethyl acetate three times. After the organic layer was dried with anhydrous magnesium sulfate, the resultant was filtrated. A residue obtained by vacuum concentration of the filtrate was refined by silica gel column chromatography (from hexane to hexane:ethyl acetate=5:5), to obtain the entitled compound (1.0 g).

(Step 10) tert-butyl 3-(4-(1,1-difluoro-2-hydroxy-2-
methylpropoxy)-7-(thiazol-2-yl)benzo[id]oxazol-2-
yl)-3,6-diazabicyclo[3.1.1]heptane-6-carboxylate The compound (92 mg) obtained in the step 9 was dissolved in tetrahydrofuran (1.7 mL), and 0.95M tetrahydrofuran solution (0.85 mL, an equivalent amount of 5) of methyl magnesium bromide was added to the resultant at 0° C. The resultant was heated to room temperature and then stirred for 1 hour, a saturated ammonium chloride aqueous solution was added to the resultant, and the resultant was subjected to extraction with ethyl acetate three times. The organic layer was dried with anhydrous magnesium sulfate, and then the resultant was filtrated. A residue obtained by vacuum concentration of the filtrate was refined by silica gel column chromatography (from hexane to hexane: ethyl acetate to ethyl acetate), to obtain the entitled compound (82 mg).

(Step 11) Synthesis of 1-((2-(3,6-diazabicyclo
[3.1.1]heptan-3-yl)-7-(thiazol-2-yl)benzo[d]oxazol-
4-yl)oxy)-1,1-difluoro-2-methylpropan-2-ol (the
Compound Represented by formula (1))

Chloroform (5.9 mL) was added to the compound (307 mg) obtained in the step 10, trifluoroacetic acid (1.4 mL) was added to the resultant at 0° C., and the resultant was stirred at 0° C. for 3.5 hours. Saturated sodium bicarbonate water was added to the reaction liquid, and the resultant was subjected to extraction with chloroform. After the organic layer was dried with anhydrous magnesium sulfate, the resultant was filtrated. A residue obtained by vacuum concentration of the filtrate was refined by amino silica gel column chromatography (from chloroform to chloroform:methanol=9:1), to obtain the compound represented by formula (1) in the form of a white solid (223 mg).

ESI-MS (m/z) 423 (M+H)$^+$ $^1$H-NMR (chloroform-d, TMS) (ppm): 1.53 (s, 6H), 1.65 (d, J=9.3 Hz, 1H), 2.82-2.87 (m, 1H), 3.90-4.01 (m, 7H), 7.23-7.25 (m, 1H), 7.44 (d, J=3.3 Hz, 1H), 7.84 (d, J=8.8 Hz, 1H), 7.94 (d, J=3.3 Hz, 1H).

Example 1

Figure 3:
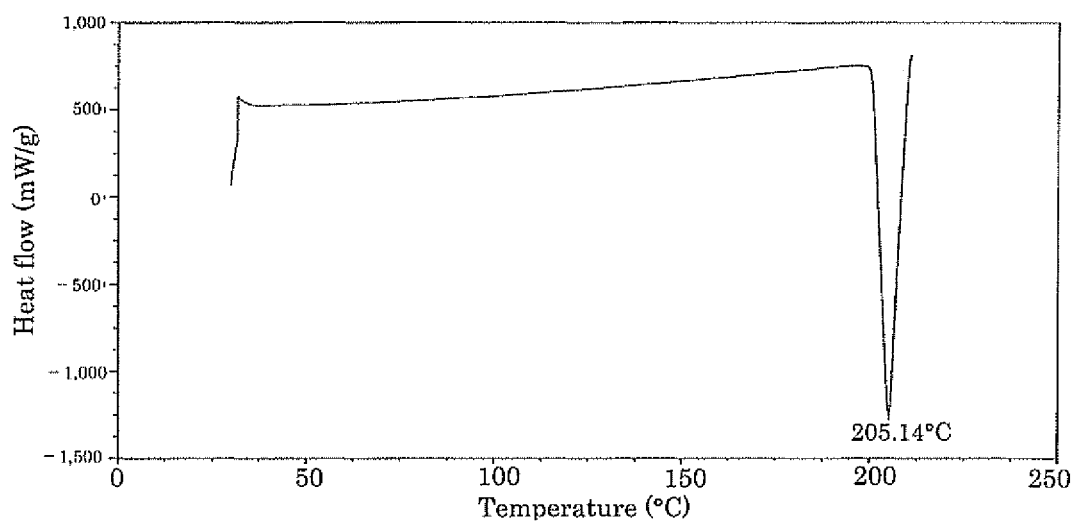
FIG. 3 plots differential scanning calorimetric (DSC) thermal analysis data of the I type crystal of the compound represented by formula (1).

A mixture solvent (1:1, v/v) (21.9 mL) of ethyl acetate and 2-propanol was added to the solid (219 mg) of the compound represented by formula (1) obtained in Referential synthesis example 1 and heated to 60° C. to dissolve the compound. This solution was concentrated to dryness to obtain a residue, to which a mixture solvent (1:1, v/v) (4.38 mL) of ethyl acetate and 2-propanol was added, and the resultant was stirred at 45° C. for 1 hour. After the resultant became room temperature, hexane (21.9 mL) was added to the resultant, and the resultant was stirred for 1 hour. After filtration, the resultant was washed with hexane and dried, to obtain the I type crystal (194 mg). The obtained I type crystal had characteristic peaks at diffraction angles (2θ±0.2°) of 7.7°, 9.4°, 13.2°, 13.7°, 14.5°, 15.7°, 17.0°, 18.9°, 19.4°, 22.9°, 23.3°, 25.7°, 28.7°, and 35.7° in powder X-ray diffraction. The powder X-ray diffraction pattern of the I type crystal is plotted in FIG. 1. As a result of a differential scanning calorimetry (DSC) analysis of the obtained crystal, an endothermic peak was observed at 205° C. Differential scanning calorimetric (DSC) thermal analysis data of the I type crystal is plotted in FIG. 3.

Example 2

Figure 2:
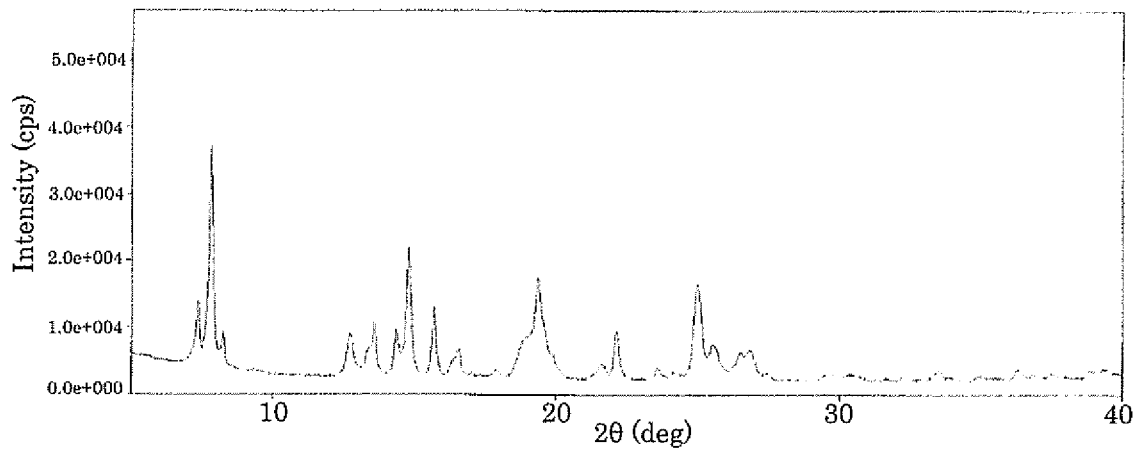
FIG. 2 plots a powder X-ray diffraction pattern of the II type crystal of the compound represented by formula (1)

Methanol (50 mL) was added to the I type crystal (584 mg) obtained in Example 1, to dissolve the I type crystal. A homogeneous solution obtained to be about one sixth the weight through vacuum concentration was cooled to 0° C. and stirred for 10 minutes, to precipitate a solid, followed by concentration to dryness to obtain a residue, to which a mixture solvent (2:1, v/v) (35 mL) of hexane and ethyl acetate was added. The resultant was stirred at room temperature for 30 minutes. After filtration, the resultant was washed with a mixture solvent (2:1, v/v) of hexane and ethyl acetate and dried, to obtain the II type crystal (566 mg). The obtained II type crystal had characteristic peaks at diffraction angles (2θ±0.2°) of 7.4°, 7.8°, 8.2°, 12.7°, 13.6°, 14.3°, 14.7°, 15.7°, 16.5°, 19.3°, 22.1°, 25.0°, and 25.6° in powder X-ray diffraction. The powder X-ray diffraction pattern of the II type crystal is plotted in FIG. 2.

Test Example 1: Evaluation of PDE4 Inhibition

The PDE4 inhibiting activity was measured in the following manner, employing Scintillation Proximity Assay (SPA). The specimen compound dissolved in dimethyl sulfoxide and diluted 10 fold with a buffer solution for reaction containing 50 mM Tris-HCl (pH of 7.4), 8.3 mMMgCl$_2$, 1.7 mM EGTA, and 3 mg/mL bovine serum albumin (BSA) was added in 10 microliters in a 96-well assay plate. After PDE4 diluted 375 fold with the buffer solution for reaction was further added in 50 microliters, a [2,8-$^3$H]-Adenosine-3',5'-cyclic phosphate triethylammonium salt diluted 1,000 fold with the buffer solution for reaction was added in 40 microliters, and the resultant was left to stand still at room temperature for 120 minutes.

Subsequently, a suspension of RNA binding YSi-SPA Beads containing 200 mM $ZnSO_4$ was added in 50 microliters, and the resultant was left to stand still at room temperature for 15 minutes, to adsorb the product of the enzyme reaction to the Beads. Subsequently, radioactivity was measured with a liquid scintillation counter for a 96-well plate. The inhibition rate of the compound represented by formula (1) to a control was calculated according to the following calculation formula, where the blank was prepared as the buffer solution for reaction only, with no enzyme preparation, and the control was prepared with the enzyme preparation and with only dimethyl sulfoxide instead of the specimen solution.

Inhibition rate (%)={1−(value obtained from addition of the specimen-value of the blank)/(value of the control-value of the blank)}×100

The PDE4 inhibiting activity (the concentration at an inhibition rate of 50%) of the specimen compound was calculated from an inhibition curve that was based on inhibition rates at various concentrations.

According to the method described above, the PDE4 inhibiting activity (the concentration at an inhibition rate of 50%) of the compound represented by formula (1) was lower than 100 nM.

Test Example 2: Stability Test

The I type crystal and the II type crystal of the compound represented by formula (1) were put in glass bottles (in about 300 mg each) and stored under various conditions. After the storage period, the chemical purity of the samples taken out was measured by HPLC. The conditions of each test were as follows.

Thermal stability test: 60° C., hermetically sealed, a period of 3 weeks
Photostability test: 25° C., 1.2 million lux hours (2,000 lux, for 25 days)
Accelerated stability test (hermetically sealed): 40° C., 75% RH*, a period of 1 month
Accelerated stability test (opened): 40° C., 75% RH*, a period of 1 month
*RH: relative humidity As the result of evaluation of each stability, the amount of the compound represented by formula (1) contained in the crystal is presented in Table 1 as a residual ratio (a HPLC area percentage ratio to the initial value, expressed in percentage).

TABLE 1

| | Residual ratio (%) of compound represented by formula (1) | |
|---|---|---|
| | I type crystal | II type crystal |
| Initial value | 100.0 | 100.0 |
| Thermal stability test | 99.8 | 100.0 |
| Photostability test | 100.1 | 99.5 |
| Accelerated stability test (hermetically sealed) | 100.1 | 100.1 |
| Accelerated stability test (opened) | 100.1 | 100.0 |

The residual ratio of the compound represented by formula (1) in each crystal form was high, and a high stability was exhibited.

Test Example 3: Hygroscopicity Test

Isothermal adsorption measurement of the I type crystal and the II type crystal of the compound represented by formula (1) was performed, using a water vapor adsorption measurement instrument (available from Surface Measurement Systems Ltd., DVS ADVANTAGE 1) (with a sample of about 10 mg, at 25° C., at from 0% RH through 95% RH).

As the result of evaluation of hygroscopicity, a weight increase rate at 95% RH (weight increase from initial value/initial value×100, *initial value: weight equilibrium value at 0% RH) is presented in Table 2.

TABLE 2

| | Weight increase rate (%) |
|---|---|
| I type crystal | 0.6 |
| II type crystal | 10.7 |

Aspects of the present invention are, for example, as follows.
<1> A crystal of 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol represented by formula (1) (a compound represented by formula (1)),

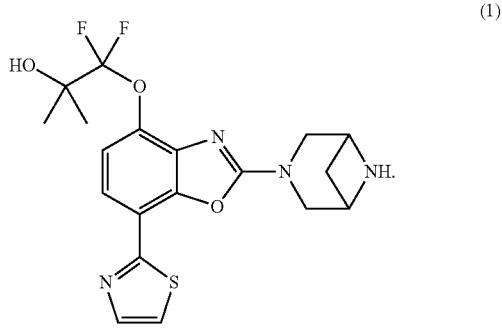 [SMILES: CC(C)(O)C(F)(F)Oc1ccc(-c2nccs2)c2oc(N3CC4CC(C3)N4)nc12]

<2> The crystal according to <1>, wherein the crystal has characteristic peaks at diffraction angles (2θ±0.2°) of 7.7°, 14.5°, 17.0°, 18.9°, 19.4°, 23.3°, and 25.7° in powder X-ray diffraction.
<3> The crystal according to <1>, wherein the crystal has characteristic peaks at diffraction angles (2θ±0.2°) of 7.7°, 9.4°, 13.2°, 13.7°, 14.5°, 15.7°, 17.0°, 18.9°, 19.4°, 22.9°, 23.3°, 25.7°, 28.7°, and 35.7° in powder X-ray diffraction.
<4> The crystal according to <2> or <3>, wherein the crystal has an endothermic peak temperature of 205±3° C. in differential scanning calorimetry (DSC).
<5> The crystal according to <1>, wherein the crystal has characteristic peaks at diffraction angles (2θ±0.2°) of 7.8°, 14.7°, 15.7°, 19.3°, and 25.0° in powder X-ray diffraction.
<6> The crystal according to <1>, wherein the crystal has characteristic peaks at diffraction angles (2θ±0.2°) of 7.4°, 7.8, 8.2, 12.7°, 13.6°, 14.3°, 14.7°, 15.7°, 16.5°, 19.3°, 22.1°, 25.0°, and 25.6° in powder X-ray diffraction.
<7> A pharmaceutical composition, including
the crystal according to any one of <1> to <6>.

INDUSTRIAL APPLICABILITY

The crystals of 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol obtained in the present invention are useful as pharmaceutical drugs because they have a high stability.

The invention claimed is:

1. A crystal of 1-((2-(3,6-diazabicyclo[3.1.1]heptan-3-yl)-7-(thiazol-2-yl)benzo[d]oxazol-4-yl)oxy)-1,1-difluoro-2-methylpropan-2-ol represented by formula (1),

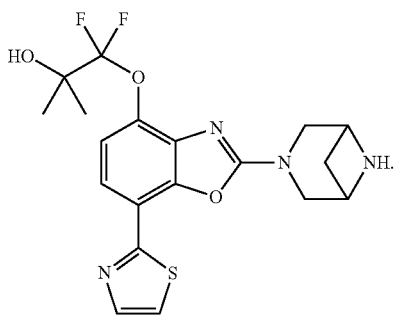

(1)

wherein the crystal has characteristic peaks at diffraction angles (2θ±0.2°) of 7.7°, 14.5°, 17.0°, 18.9°, 19.4°, 23.3°, and 25.7° in powder X-ray diffraction; or
wherein the crystal has characteristic peaks at diffraction angles (2θ±0.2°) of 7.8°, 14.7°, 15.7°, 19.3°, and 25.0° in powder X-ray diffraction.

2. The crystal according to claim 1, wherein the crystal has characteristic peaks at diffraction angles (2θ±0.2°) of 7.7°, 14.5°, 17.0°, 18.9°, 19.4°, 23.3°, and 25.7° in powder X-ray diffraction.

3. The crystal according to claim 1, wherein the crystal has characteristic peaks at diffraction angles (2θ±0.2°) of 7.7°, 9.4°, 13.2°, 13.7°, 14.5°, 15.7°, 17.0°, 18.9°, 19.4°, 22.9°, 23.3°, 25.7°, 28.7°, and 35.7° in powder X-ray diffraction.

4. The crystal according to claim 2, wherein the crystal has an endothermic peak temperature of 205±3° C. in differential scanning calorimetry (DSC).

5. The crystal according to claim 1, wherein the crystal has characteristic peaks at diffraction angles (2θ±0.2°) of 7.8°, 14.7°, 15.7°, 19.3°, and 25.0° in powder X-ray diffraction.

6. The crystal according to claim 1, wherein the crystal has characteristic peaks at diffraction angles (2θ±0.2°) of 7.4°, 7.8°, 8.2°, 12.7°, 13.6°, 14.3°, 14.7°, 15.7°, 16.5°, 19.3°, 22.1°, 25.0°, and 25.6° in powder X-ray diffraction.

7. A pharmaceutical composition, comprising:
the crystal according to claim 1.

* * * * *